United States Patent [19]
Jungfer et al.

[11] Patent Number: 5,114,847
[45] Date of Patent: May 19, 1992

[54] PROCESS FOR THE PRODUCTION OF PERMANENTLY CULTURABLE ANIMAL AND HUMAN CELL LINES AND THE USE THEREOF

[75] Inventors: Herbert Jungfer; Heinrich Barchet, both of Tutzing; Winfried Albert, Pähl, all of Fed. Rep. of Germany

[73] Assignee: Boehringer Mannheim GmbH, Mannheim, Fed. Rep. of Germany

[21] Appl. No.: 590,602

[22] Filed: Sep. 25, 1990

Related U.S. Application Data

[63] Continuation of Ser. No. 784,696, Oct. 3, 1985, abandoned, which is a continuation of Ser. No. 490,094, Apr. 29, 1983, abandoned.

[30] Foreign Application Priority Data

May 4, 1982 [DE] Fed. Rep. of Germany ....... 3216650
Dec. 9, 1982 [DE] Fed. Rep. of Germany ....... 3245665

[51] Int. Cl.$^5$ ............................ C12P 1/00; C12N 5/00
[52] U.S. Cl. .................................. 435/41; 435/240.26
[58] Field of Search ............... 435/69.6, 240.27, 172.1, 435/172.3, 41, 240.26; 436/548; 935/93, 96, 99–104, 52–54

[56] References Cited

U.S. PATENT DOCUMENTS

| | | | |
|---|---|---|---|
| 4,172,124 | 10/1979 | Koprowski et al. | 435/172.1 |
| 4,224,404 | 9/1980 | Viza | 435/68 |
| 4,394,448 | 7/1983 | Szoka, Jr. et al. | 435/317 |
| 4,464,465 | 8/1984 | Lostrom | 435/172.2 |
| 4,465,769 | 8/1984 | Hampar et al. | 435/948 |
| 4,537,852 | 8/1985 | Sugimoto | 935/99 |

FOREIGN PATENT DOCUMENTS 8300164 1/1983 PCT Int'l Appl. ................... 435/68

OTHER PUBLICATIONS

Cassingena, et al., Transformation of Normal Diploid Cells by Isolated Metaphase Chromosomes of Virus-transformed . . . Gene, vol. 4, pp. 337-349, 1978.
Shay, et al., Nuclear Control of Tumorigenicity in Cells Reconstructed by PEG-Induced Fusion of Cell Fragments, J. Supramolecular Structure, vol. 11, pp. 33-49, 1979.
Howell, et al. Tumorigenicity and its Suppression in Cybrids of Mouse and Chinese Hamster Cell Lines, Proc. Natl. Acad. Sci. USA, vol. 75, No. 5 pp. 2358-2362, 1978.
Vedmett, et al., Reconstruction of Mammalian Cells from Nuclear and Cytoplasmic Components Separated by Treatment . . . , Proc. Natl. Acad. Sci. USA, vol. 71, No. 5, pp. 1999-2002, 1974.
Olsson, et al., Human-Human Hybridomas Producing Monoclonal Antibodies of Predefined Antigen Specificity, Proc. Natl. Acad. Sci. USA, vol. 77, No. 9, pp. 5429-5431, 1980.
Harris, H. et al., Feb. 13, 1965, Nature 205:640-646.
Bruno, J. et al., Dec. 1981, Mol. Cell. Biol. 1:1163-1176.
Jonak, Z. L., et al., Feb. 6, 1983, Hybridoma 2:124.
Hightower, J. H.,: 1982 in Techniques in Somantic Cell Genetics CL19, Plenum Press.
Prujansky-Jakobovits et al, "Alteration of Lymphocyte Surface Properties by Insertion of Foreign Functional Components", Proceedings of the National Academy of Sciences 77(12), pp. 7247-7251 (1980).
Veomett et al, "Reconstruction of Mammalian Cells from Nuclear and Cytoplasmic Components Separated by Treatment with . . . ", Proceedings of the National Academy of Sciences 71(5) pp. 1999-2002 (1974).
Kozbor et al, "Human Hybridomas Constructed with Antigen Specific EBV . . . ", Proceedings of the National Academy of Sciences 79 pp. 6651-6655 (1982).
Shih et al, "Passage of Phenotypes of Chemically Transformed Cells Via Transfection of DNA and Chromatin", Proceedings of the National Academy of Sciences 76(11) pp. 5714-5718 (1979).

*Primary Examiner*—John Doll
*Assistant Examiner*—George C. Elliott
*Attorney, Agent, or Firm*—Felfe & Lynch

[57] ABSTRACT

A method for obtaining permanently culturable human and animal cell lines, as well as uses for these cell lines, are disclosed. The method involves fusing cells of a non-immortal cell line with cytoplasts or cytoplasma fractions of "immortal", transformed cells such as immortal myeloma cells, ascites-tumor cells or Epstein Barr Virus infected cells. Once fusion takes place the product is a permanently culturable variant of the previously normal cell line.

7 Claims, No Drawings

PROCESS FOR THE PRODUCTION OF PERMANENTLY CULTURABLE ANIMAL AND HUMAN CELL LINES AND THE USE THEREOF

This application is a continuation, of application Ser. No. 784,696, filed Oct. 3, 1985, now abandoned, which is a continuation of application Ser. No. 490,094, filed Apr. 29, 1983, now abandoned.

The present invention is concerned with a process for the production of permanently culturable animal and human cell lines and with the use of the cell lines so obtained for obtaining cell products.

Attempts have long been made, not only for scientific but also for practical reasons, to permanently culture human and animal cells independently of normal animal and human tissues. Hitherto, this has not been successful and only in a few special cases has it been possible to achieve permanent culturability in the case of certain blood cells.

For the production of monoclonal antibodies with definite antigen binding specificity, it is known to use the so-called hybridoma technique. With this process, which was developed by Köhler and Milstein (Continuous culture of fused cells secreting antibody of predefined specificity, Nature, 256,495–497/1975), an individual, antibody (AB)-forming cell can be made potentially "immortal" and can be multiplied as desired. By the fusion of the AB-forming cells (B-lymphocytes) with a malignant degenerated cell (myeloma), cell hybrids can be produced which combine the properties of both parent parts: the ability to produce antibodies and the ability for permanent growth. The new term "hybridoma" was formed by the fusion of the words hybrid cells and myeloma.

For a better understanding of the special features of this technique, some fundamentals of the structure and synthesis of antibodies (immunoglobulins, Ig) will now be described. An Ig molecule is composed of two identical light (L) chains and two identical heavy (H) chains. Each H and L-chain is divided up genetically and functionally into different sections, the so-called variable regions which display a much higher degree of sequence heterogeneity than the parts referred to as constant regions. The combining sites of the antibody are developed in the variable regions. The multiplicity of the amino acid exchange produces a large repertoire of three-dimensional structures which, in their form, are complementary to a large number of antigens. It is estimated that a mammal form between $10^6$ and $10^7$ different body combining sites.

Antibodies are a synthesis product of B-lymphocytes. During the ontogenetic development of a B-cell from a parent cell, one of the many available variable region genes is combined with one of the comparatively few constant region genes, not only for the L-chain but also for the H-chain. As soon as the gene association has taken place, the B-cell in question is programmed only to be able to produce a single type of antibody molecule and this programming is inherited by its daughter cells. Without antigen stimulus, the B-cell persists in a quiescent state, without proliferating. It produces and secretes only a little immunoglobulin but, in its cell membrane, carries firmly anchored antibodies which have exactly the same antigen combining sites as the secreted antibodies. If an antigen penetrates into the organism, it is presented to the B-cells in a series of complex cellular interactions.

The B-cell, the membrane immunoglobulin of which reacts specifically with the antigen, is induced to divide and to form a clone of daughter cells which differentiate into antibody-producing cells (plasma cells). Since a B-cell clone forms antibodies with identical structure and with identical antigen combining sites, the product of such a clone is called a "monoclonal antibody". Complex constructed antigens, such as proteins, microorganisms or cells, contain many different antigen-effective sites (determinants, epitopes) and consequently many different B-cells are stimulated to divide and to form clones. Therefore, a large number of antibodies are formed which, with regard to their size, charge, specificity and affinity, differ and appear together in the immune serum. However, the immune response directed against a single determinant is, as a rule, also polyclonal. It is known that mice can form up to $10^3$ different antibodies against a simple hapten, i.e. an isolated determinant. These facts make it clear that it is extremely difficult, if not impossible, to produce antisera against a particular antigen in a reproducible manner. Therefore, for many years, attempts have been made to find a process which permits individual B-cells to expand clonally in order, to obtain homogeneous, monoclonal antibodies. The natural precursors were the myelomas or plasmacytomas, which have long been known cause malignant diseases in mice, rats and humans. A myeloma arises when a B-cell degenerates malignantly and proliferates uninhibitedly, the clone of the daughter cells thereby producing large amounts of homogeneous antibodies. Myelomas can be induced in certain inbred mice strains by chemical manipulation. All attempts to obtain monoclonal antibodies with known antigen-binding specificity by combination of hyperimmunisation and myeloma induction have, however, been unsuccessful. However these attempts resulted in myeloma cell lines which could be cultured in vitro and have become the basis of the hybridoma technology. The fundamental idea of Milstein and Köhler was to produce a hybrid cell by fusion of normal B-cells from immunised animals with a culturable and permanently growing myeloma cell.

In their first experiments, they fused the myeloma cells with the lymphocytes from the spleen of a mouse which had been immunised with sheep erythrocytes. They obtained 10 viable hybrids, two of which formed antibodies with specificity against sheep erythrocytes. The antibody-producing hybrids resembled the myeloma cells insofar as they grew continuously in culture and formed tumours when they were implanted into syngenic mice. Furthermore, it was of great practical importance that the hybrid cells, like myeloma cells, could be stored in liquid nitrogen and kept alive for long periods of time.

Technique of hybridoma production

Mice are immunised with antigen as in the case of conventional antiserum production, usually repeated with interruptions of several weeks. Immediately before the fusion, the mouse is sacrificed and its spleen removed under aseptic conditions. The spleen sac is incised and the spleen pulp carefully pressed out. The spleen lymphocytes (about $10^8$ cells) are suspended in cell culture medium and mixed with myeloma cells in a ratio of 1:1 to 10:1. The cell mixture is packed tightly on to the bottom of a tubelet by centrifugation and, after removal of the liquid supernatant, treated with a fusion medium (30 to 50% polyethylene glycol solution or suspended, inactivated Sendai virus). After washing out the fusion medium, the cell mixture with a cell density of about $10^6$ cells per ml is transferred to sterile culture vessels or plates and cultured in a carbon dioxide-gassed incubator. 2 to 4 weeks. after fusion, the growth of the hybridoma clones is microscopically visible From this point of time, the culture supernatant can be investigated for the presence of antibodies with the desired specificity. For this purpose, analysis processes are necessary which can detect antibodies in the submicrogram range (RIA, ELISA, immunofluorescence). The cells from positive part cultures are then cloned, i.e. individual cell cultures are applied. Isolated clones, which form the "correct" antibodies, are expanded and, for tumour induction, injected into the abdominal cavity of pristane-pretreated syngenic mice (as a rule Balb/c-inbred mice). 6 to 20 days after the inoculation, in the case of initiation of the tumour, homogeneous antibodies can be obtained from the blood or preferably from the abdominal cavity (ascites) (with a yield of 50 to 150 mg. monoclonal antibodies per mouse).

After the fusion, a very heterogeneous mixture of hybrids and non-fused cells is present. In the case of the use of $10^8$ mouse spleen cells, there can be a maximum of $10^3$ viable hybridoma cells. Since the hybrid cells require a certain start up time before they are able to commence proliferation but the non-fused myeloma cells immediately grow further, a selection process must ensure the survival of the few hybridomas. The standard selection process in the hybridoma technique is based upon the so-called HAT selection medium (J. W. Littlefield: Selection of hybrids from mating of fibroblasts in vitro and their presumed recombinants, Science, 145, 709–710/1964). A stands for aminopterin, a folic acid antagonist, which blocks the main path of the DN synthesis. Normal cells can circumvent the aminopterin block with the help of thymidine kinase (TK) and hypoxanthine-guanine-phosphoriboyltransferase (HGPRT) insofar as thymidine (T) and hypoxanthine (H) are available in the culture medium. If a cell is missing one of the two enzymes, then it is not viable in the HAT medium. Therefore, for the hybridoma development, mutants of the myeloma cells are used which are TK or HGPRT deficient. These cells are then only viable in the HAT medium if they are fused with a normal cell which, with its gene pool, introduces the missing enzyme into the hybrid cell. The non-fused lymphocytes of the spleen have a naturally limited period of life in the culture and, therefore, do not represent a threat to the hybridoma.

In the case of the production of hybridomas, the following problems arise:

1. HAT medium selection

The selective suppression of the growth of nonfused myeloma cells is, as described above, an essential prerequisite for the production of hybridoma clones. However, the HAT selection is, even for normal, non-deficient cells, an extremely nonphysiological process which impairs the ability of the cells to divide and survive. Especially in the case of human lymphocytes, it is extremely difficult to adjust the components of the HAT medium with regard to concentration so that HGPRT-negative cells are dependably killed but HGPRT-positive cells can survive.

The disparity between the number of the introduced lymphocytes and myeloma cells, on the one hand, and the yield of multipliable hybrids, on the other hand, is illustrated by the following figures: in the case of the introduction of $10^8$ mouse lymphocytes into a typical fusion batch, 500 hybridoma clones are generally regarded as being a good result. Since in the spleen of a mouse, even when it has been repeatedly (hyper)immunised, only one antibody against the immunogen is formed from $10^3$ to $10^4$ cells (as has been demonstrated by means of the Jerne plaque technique: N. V. Jerne and A. A. Nordin, Science, 140, 405/1963), in the case of purely random hybridoma formation, $10^3$ to $10^4$ clones are required in order to be able to expect only one clone with the desired antibody specificity. In the case of the production of human hybridomas, the disparity is even more striking: it is regarded as being a good result when, per fusion, 4 to 10 hybrid clones are obtained.

2. Chromosome losses

After a fusion has been successfully carried out, the newly formed hybrid cells must be finished with about double the amount of chromosomes originally provided by nature. As practical experience has shown, hybrid cells tend to "lose" chromosomes. In the case of each cell division, in the case of the nonphysiological excess amount of chromosomes, there is the danger that these are not distributed uniformly to the two daughter cells. The daughter cell which gets less of the excess and, therefore, is not maintained with "luxury" productions, has, in relationship with the other, a selection advantage and becomes the dominant cell of the culture. However, the synthesis of immunoglobulin is not essential for the viability of the hybrid cell but rather represents a "luxury" synthesis ability. The appearance of non-producer variants in a hybridoma clone is, therefore, a frequent occurrence and requires laborious recloning measures in order to ensure the production ability of a clone. The tendency to lose chromosomes is especially present in the case of interspecies hybrids.

3. Hybrid immunoglobulins

Myeloma cells are malignant B-cells and themselves form immunoglobulins (with unknown antigenbinding specificity). The myeloma cell introduces this ability into the hybridoma in the same way as normal B-cells. Since the different chains of the Ig molecule are synthesised separately and are only subsequently combined to give the complete antibodies, in a hybridoma cell in which the two different L- and H-chains are synthesised, there randomly result 10 different combinations of which the desired "correct" antibodies only account for 1/16th of the total, amount of Ig. Therefore, with great expense, mouse myeloma cell mutants have been developed which themselves do not form H- or L-chains. However, for the fusion of human lymphocytes, hitherto there has not been available a similar and considerably developed myeloma line.

Even more serious problems are present in the case of the alternatives to the hybridoma technique:

1. Immortalisation of B-lymphocytes by viruses

Human B-lymphocytes of normal donors can be malignantly transformed by infection with Epstein-Barr virus (EBV). The EBV-infected, lymphoblastoid cells can be continuously cultured and cloned in vitro. However, in comparison with hybridoma-produced EBV lymphoblastoid lines, one obtains only 1/10th or less of immunoglobulins, together with unsatisfactory production stability. It is assumed that B-cells are fixed by EBV in an early stage of differentiation and, therefore, clones are frequently obtained overproportionally which produce IgM in very small amounts.

In an analogous manner, mouse B-lymphocytes can be transformed by the Abelson mouse leukemia virus (MuLV). Here, too, the lymphocytes are unfavourably fixed in an early stage of differentiation and are poor producers of antibodies.

2. Long-term cultures of non-transformed B-lymphocytes

The most recent publications (B. Spredni et al.: Long-term culture and cloning of non-transformed human B-lymphocytes, J. Exp. Med., 154, 1500–1516/1981; M. Howard et al., Long-term culture of normal mouse B-lymphocytes, Proc. Natl. Acad. Sci. U.S.A. in the press) demonstrate the possibility of culturing and cloning B-lymphocytes without transformation by special culture conditions (permanent mitogenic stimulation; lymphokine-conditioned media etc.) permanently. However, these processes are at present not suitably certain for a routine production of monoclonal antibodies.

The prior art can, therefore, be summarised in the following way:

B-lymphocytes of normal donors can be artificially "immortalised". The hybridoma technique uses living myeloma cells which, in a culture, have an unlimited ability to multiply, which are fused with antigen-stimulated B-lymphocytes. The hybrid cells obtained by cell-cell fusion are isolated by HAT selection and cloned by application of individual cell cultures. Hybridoma clones which form antibodies with the desired specificity are multiplied for the mass production of monoclonal antibodies. However, considerable disadvantages arise from the HAT selection, by chromosome losses and hybrid immunoglobulins.

In another process, B-lymphocytes are malignantly transformed by infection with special viruses and converted into permanently growing cells, with maintenance of antibody synthesis. However, they are notoriously weak antibody producers.

With regard to the mass production of monoclonal antibodies with definite antigen-binding specificity, the hybridoma technique is, therefore, clearly superior to the present alternative processes.

However, the hybridoma technique also has serious disadvantages. The most important disadvantage is that the process is, on the one hand, limited to HAT-sensitive fusion partners and, on the other hand, to few types of cells, namely, lymphocytes and nerve cells.

It is an object of the present invention to eliminate these disadvantages and to provide a new and advantageous process for the production of permanently culturable animal and human cell lines.

Thus, according to the present invention, there is provided a process for obtaining permanently culturable animal and human cell lines by fusion of normal animal and -human cells with biological components which allow culturing of cell lines in vitro, wherein normal animal or human cells are fused with cell fragments of transformed cells which alone are not capable of multiplication, and are then cultured in a culture medium without selection substances.

It is important, in the case of the process according to the present invention, that the fragments used for the fusion are completely free of cells which are even more capable of multiplying and which can no longer multiply.

Surprisingly, in the case of the process according to the present invention, the preponderant amount of the cytoplasma portion of the non-degenerated partner, i.e. of the normal cell, does not lead to an extinction of the malignant properties of the degenerated cells and thus to a loss of the ability for permanent growth, although it is known that by fusion of transformed cells with normal cytoplasm from non-malignant cells, the malignancy i-s expunged (W. J. Shay et al., Suppression of tumorgenicity in Hybrids, J. Supramol St. Cell Biochem., 16, 75–82/1981). In addition, it was not certain whether the cell nuclei would combine with the isolated nuclei of the degenerated cells, e.g. with myeloma nuclei, to give a common genome when the myeloma cytoplasma was also not introduced into the hybrid.

The fusion takes place according to known methods, preferably in the presence of fusiogenic substances, preferably polyethylene glycol or Sendai virus since, in this way, analogously to the hybridoma technique, an increase of the fusion yield is brought about. Other fusiogenic substances are known and can also be used.

The fragments of the transformed cells, for example of the myeloma cells, can be obtained by known methods. The cell wall is preferably ruptured by lysis or mechanically. The nuclear fraction can then possibly be separated from the cytoplasm fraction by centrifuging and the fractions used alone. The lysis of the cells is accomplished, preferably the cells to swell in glycerol and subsequent introduction into glycerol-free buffer solution. This leads to a bursting of the cell membranes. Another preferred method is of production of karyoplasts and cytoplasts by treating the cells with cytochalasin B, a commercially available antibiotic. This process is known from Biochem. Biophys. Res. Comm., 63, 669–674/1975. In this process a kind of "cell division" takes place, yielding (i) cell nucleus surrounded by the cell membrane, i.e., a caryoplast, and (ii) nucleus free cytoplasm, also surrounded by a membrane, i.e., a cytoplast. In the scope of the present invention, both prove to be equally suitable for the fusion, like the cell fragments or nuclei or cytoplasm fractions obtained by lysis or mechanically, which are no longer enclosed by a cell membrane. The mechanical digestion can be carried out by well-known methods which do not need to be explained here.

By transformed cells are meant those which, in vitro and in vivo, no longer obey normal growth regulation mechanisms. Examples thereof include malignantly transformed cells, for example cancer cells, cells transformed by virus infection (for example Epstein-Barr virus) and cells changed by cancinogenic substances.

If cell fractions are used for the process according to the present invention, then these do not have to be completely pure but they must not contain any intact cells still capable of multiplying.

An important characteristic of the present invention is that the hybrids obtained are not exposed to the competition of transformed, nonhybrid, in vitro culturable cells and, therefore, their growth must also not be suppressed by HAT selection substances. In this way, the very disadvantageous influence of the HAT selection medium on the hybrids is overcome and a considerable improvement of the yields and of the viability of permanently culturable cells is obtained.

Furthermore, according to the present invention, for the hybrid formation it is no longer a prerequisite to use a HAT-sensitive cell as transformed cell. There are many permanently-growing cell lines which do not display HAT sensitivity and which could not be used for the conventional hybridoma technique but which can be employed in the scope of the present invention for the production of the fragments for the fusion.

Cells are induced to "extrude" their nucleus into an extreme protuberance by cytochalasin B (a fungal metabolite). Under the influence of gravitational forces, for example centrifugation, the thin connection is easily torn off. In this manner, a nucleus-free cell body (cytoplast) and a nucleus which is enveloped with cell membrane and a narrow cytoplasmic fringe (karyoplast or minicell) result. Neither karyoplasts nor cytoplasts are capable of multiplying but maintain their special functions for a period of from several hours to days. The nucleus extrusion requires a relatively high concentration of cytochalasin B and is, so long as the connection is not torn off, fully reversible. Lower concentrations of cytochalasin B suppress the cell division by mitosis, without nucleus extrusion. The standard method for the cytoplast/karyoplast production for non-adherent cells has been described by M. H. Wigler and I. B. Weinstein: A preparative method for obtaining enucleated mammalian cells, Biochem. Biophys. Res. Comm., 63, 669-674/1975.

Furthermore, it has been ascertained that not only the above-mentioned B-lymphocytes but also all other hitherto investigated animal and human cells can be "immortalised" according to the present invention (see Examples 6 to 8). Thus, different types of cells, such as T-lymphocytes (carriers of the cellmediated immunity and regulator cells of the immune system), endothelial cells (wall cells from human umbilical veins) and melanoma cells (isolated from cryo-preserved tumour metastasis material) are converted, by the method according to the present invention, into permanent growth (immortalised).

Thus, the process according to the present invention makes it possible to place any desired human or animal cells into a culture and, in this manner, also to solve the problem of producing cell products in vitro, for example antibodies, coagulation factors, enzymes and other substances synthesised by the cell. The cultures according to the present invention also make it possible to avoid having to use experimental animals to a considerable extent for testing chemical substances.

The present invention is also concerned with the use of a permanently culturable cell line produced by the process according to the present invention for obtaining cell products, such as monoclonal antibodies, coagulation factors, lymphokines, enzymes and other cell products such as proteins or other groups of substances.

In particular, this embodiment of the present invention can be used in the case of the use of permanently culturable B-lymphocytes for the production of monoclonal antibodies, in the case of the use of permanently culturable endothelial cells, melanoma cells, hepatocytes, kidney cells and the like for obtaining coagulation factors, in the case of the use of permanently culturable T-lymphocytes B-lymphocytes and/or macrophages for obtaining lymphokines and in the case of permanently culturable glandular cells for obtaining products secreted by glands, such as hormones and the like. It will be appreciated that, depending upon the nature of the animal cells used according to the present invention for the immortalisation, there can be obtained all interesting cell products so that it is not necessary to describe these here in detail.

The permanently culturable cells according to the present invention can, furthermore, as already mentioned, also be used for testing active substances. Furthermore, the immortalised cells obtained according to the present invention can be used as a source for genetic information which codes for the expression of desired cell products in such a manner . that the component of the immortalised cell carrying the genetic information, thus its genome, part of the genome or RNA, is obtained and transformed according to the methods of gene manipulation into an appropriate micro-organism and the desired cell product obtained from the latter.

According to an embodiment of the method of the present invention, the production of the cell products, such as the monoclonal antibodies and other cellular substances, can also take place in such a manner that the hybrid cells formed are not cultured directly for the cell product formation or substance synthesis but rather their genome or parts of the genome or RNA are transformed according to the methods of gene manipulation into an appropriate micro-organism and the latter are cultured to obtain the monoclonal antibody or the cellular substances. In the case of this embodiment of the present invention, the genome of the hybrid cell is isolated by the methods known for this purpose and the genome is transformed with the help of a suitable vector, for which purpose the commercially available vectors can be used, according to the standard methods developed for this-purpose, into an appropriate micro-organism.

The transformed micro-organism is then cultured in the usual manner and the desired cell product obtained from it. As micro-organism, there is preferably used one of those strains of *Escherichia coli* which have proved to be useful for gene manipulation.

The following Examples are given for the purpose of illustrating the present invention, the following abbreviations and product designations thereby being used therein:

| | |
|---|---|
| AB | antibody |
| Ig | immunoglobulin |
| H- or L-chain | "heavy" or "light" protein chain of Ig molecules |
| pristane | 2,6,10,14-tetramethylpentadecane |
| HAT selection medium | culture medium containing hypoxanthine, aminopterin and thymidine |
| TK | thymidine kinase |
| HGPRT | hypoxanthine-guanine-phosphoribosyl-transferase |
| EBV | Epstein-Barr virus |
| MuLV | Abelson mouse leukemia virus |
| CB | cytochalasin B antibiotic (Aldrich Biochemicals, Milwaukee, U.S.A.) |
| DMSO | dimethyl sulphoxide |
| DMEM | Dulbecco's minimal essential medium |
| FCS | fetal calf serum |
| Ficoll | polymeric cane sugar (Pharmacia) |
| PEG | polyethylene glycol |
| PBS | phosphate-buffered saline |
| POD | peroxidase |
| ABTS | ammonium salt of 2,2'-azino-di-(3-ethylbenzothiazoline-6-sulphonic acid) |
| EBSS | Earle's balanced salt solution |
| RPMI 1640 | Rosewell Park Memorial Institute (medium) |
| tris | tris-(hydroxymethyl)-aminomethane |
| PBL | peripheral blood lymphocytes |
| MNC | mononuclear cells (lymphocytes, monocytes) |
| hTSH | human thyroid-stimulating hormone |
| β-hTSH | β-chain of hTSH |
| FA | Freund's adjuvant |
| CFA | complete Freund's adjuvant |
| IFA | incomplete Freund's adjuvant |

| | |
|---|---|
| Methocel 1500 | methylcellulose (Fluka) |
| CMV | cytoplasma-membrane vesicle |
| FITC | fluorescein isothiocyanate in spheroidal |
| Covaspheres | form (Covalent Technicals, Ann Arbor, Mich., U.S.A.) |
| EAC | Ehrlich ascites cells (ATCC; CCL 77). |

EXAMPLE 1

A. Production of caryoplasts and cytoplasts from mouse myeloma cells of the line P3X63 Ag 8.653 ATCC No. CRL-1580 (analogous to the method described by M. H. Wigler and I. B. Weinstein: A preparative method for obtaining enucleated mammalian cells, Biochem. Biophys. Res. Comm., 63, 669–674/1975).

A.1. Materials

Cytochalasin B (CB, Aldrich Biochemicals, Milwaukee, U.S.A.) was dissolved in dimethyl sulphoxide (DMSO, Merck) (2 mg./ml.) and stored as a stock solution at 4° C.

Ficoll-400 (Pharmacia; polymeric cane sugar) was dissolved in redistilled water (1 g./ml.), autoclaved and stored as a 50% stock solution at −20° C.

Simple and double concentrated Dulbecco's minimum essential medium (DMEM), fetal calf serum (FCS), L-glutamine (200 mMol/liter), streptomycin-penicillin of Boehringer Mannheim GmbH.

Cellulose nitrate tubelets [centrifuge tubes[ were sterilised by ultra-violet irradiation.

Myeloma cell line Ag 8.653 ATCC CRL-1580: the line is described by J. F. Kearney et al., in "A new mouse myeloma cell line that has lost immunoglobulin expression but permits the construction of antibody-secreting hybrid cell lines, J. Immunol., 123-, 1548–1550/1979. It is azaguanine-resistant and HAT-sensitive and synthesises neither H- nor L-Ig chains. It is kept in DMEM+15% FCS+glutamine+penicillin-streptomycin +pyruvate (DMEM full medium) at 37° C. in 7% carbon dioxide atmosphere.

A.2. Methods

Enucleation: $8 \times 10^7$ Ag 8.652 cells were centrifuged for 5 minutes at $10^3$ r.p m. and resuspended in 12 ml of a 12.5% Ficoll-DMEM-CB-DMSO solution until a suspension free of cell lumps had been produced. 3 ml amounts of the cell suspension were layered on to Ficoll gradients prepared 4 and 12 hours previously and additional 2 ml Ficoll-free DMEM-CM-DMSO solution was over layered. The tubelets with the gradients were centrifuged in an ultracentrifuge for 60 minutes at 25000 r.p.m. (31° C. ).

After completion of the centrifuging, the macroscopically visible fractions ("bands") were separately collected from above with the help of an injection syringe with a long canule, each diluted in 20 ml. of culture medium (DMEM without additives), sedimented by centrifuging and resuspended in fresh DMEM.

The following four fractions were obtained:
a) cell debris on the limit between 0 and 12.5% Ficoll,
b) nucleus-free cytoplasts in the range from 15 to 16% Ficoll,
c) nuclei without recognisable plasma edge and about 2% nucleus-free cells on the limit between 17 and 25% Ficoll,
d) nucleus-containing cells, intact according to morphological criteria, with readily recognisable plasma edge and a few nuclei without plasma edge as sediment on the bottom of the tubelets.

The cell count showed that of the $8 \times 10^7$ Ag 8.653 cells, in b) there were $1.25 \times 10^6$ cytoplasts in c) $4 \times 10^6$ karyoplasts and in d) $1.1 \times 10^7$ probably intact cells.

B) Fusion of mouse spleen cells with isolated myeloma caryoplasts, cytoplasts and sediment cells from Experiment A.

B.1 Material

Fusion agent 20 g. polyethylene glycol (PEG-4000) were melted in an autoclave, cooled to 56° C. and mixed at this temperature with 20 ml. DMEM.

HAT selection medium: to DMEM full medium were added $4 \times 10^{-7}$M aminopterin, $1 \times 10^{-4}$M thymidine and $3.1 \times 10^{-5}$M hypoxanthine.

Culture vessels: tissue culture cluster 24 and cluster 96 of the firm Costar, Cambridge, Mass., U.S.A.

B.2. Methods

Fusions: The fractions b), c) and d) prepared in experiment A were mixed in separate batches with spleen cells in the ratio of 10:1 and sedimented by centrifuging. To the sediment was added 0.8 ml 50% PEG solution (at 37° C., uniformly spread over 1 minute, with continuous, gentle shaking) and then 5 ml. DMEM (at ambient temperature, uniformly over 5 minutes). After the addition of a further 20 ml. DMEM, the cells were sedimented, resuspended in fresh DMEM full medium (5 ml.) and distributed in each case on to 10 24 Costar spot tissue culture vessels coated with "feeder cells". The individual cultures were "fed" on day 1, 2, 3, 5, 7, 10 and 13 with DMEM full medium.

Feeder cells (abdominal cavity macrophages): on the day before the fusion, inbred mice (Balb/c) were sacrificed by cervical dislocation. Under sterile conditions, 4 to 5 ml. PBS were injected into the abdominal cavity and, after 1 minute, again withdrawn. The rinsed out cells were washed with DMEM, suspended in full medium at a density of $2 \times 10^5$ cells per ml. and distributed in 0.5 ml. portions on 24 Costar spot plates.

Spleen cells: Immediately before fusion, a Balb/c mouse had its spleen extirpated under aseptic conditions and the cells thereof were suspended in DMEM. Cell aggregates and tissue fragments were filtered off with muslin gauze.

ELISA on mouse immunoglobulin: microtiter plates were coated with mouse Ig antibodies from sheep (Ig fraction; 10 μg./ml. 0.9% sodium chloride solution; 150 μl. antibody solution per spot [well]). 100 μl. amounts of culture supernatant were pipetted into the coated spots and incubated for 1 hour at ambient temperature. After aspirating the supernatant and washing twice, the spots were provided with 100 μl. anti-mouse Ig-POD conjugate solution (same antibodies as above; covalently bound with horseradish peroxidase) and incubated for 1 hour at ambient temperature. After washing three times, per spot there were pipetted 100 μl. substrate solution (ABTS) and the colour development was determined photometrically.

B.3 Results

The cytoplast, caryoplast and sediment fractions prepared according to A were fused in parallel with spleen cells of a Balb/c mouse and each divided up into 10 1 ml. cultures. In each case, 5 of the part cultures were fed *without HAT additive (Plate I) and 5 were fed with HAT additive (Plate II).

Up to day 21 after fusion (a.f.), in none of the spots was the growth of lymphoid cells detectable either macroscopically or microscopically, with the exceptions of spots 4A, 4B, 4C, 3C and 3D on Plate I, which had received the fusionate of the sediment fraction without HAT medium. In these spots, already 5 days after fusion (a.f.), colonies were recognisable, which enlarged rapidly. On day 8 a.f., HAT medium was added to these spots: within 4 days thereafter, all visible colonies had died off.

From day 27 a.f., initially individual and then in almost all- spots colonies were visible, which consisted of large, spheroidal, transparent, nonadherently growing cells. On day 65 a.f., with the exception of I-3B, II-1A, II-4A, all spots were occupied with multiple colonies of lymphoid cells. The testing on this day of the culture supernatants for the content of mouse Ig showed, as indicated in the summary in the following Table 1, positive to strongly positive values in the ELISA in all part cultures with the exception of the above-mentioned colony-free spots:

TABLE 1

ELISA for the detection of mouse immunoglobulin in the culture supernatants of experiment B (65 days after fusion).

plate I: without HAT
(exceptions: 4A, 4B, 4C, 3C, 3D: + HAT, day 8 to 15)

|   | 1 | 2 | 3 | 4 | 5 | 6 |
|---|---|---|---|---|---|---|
| A | 664 | 601 | 706 | 632 |   |   |
| B | 526 | 766 | 011 | 633 |   |   |
| C | 576 | 769 | 855 | 623 |   |   |
| D | 794 | 1500 | 791 |   |   |   |

↑ ↑ ↑
1 2 3

1 = cytoplast fusion
2 = caryoplast fusion
3 = sediment cell fusion plate II: with HAT (day 1 to 14)

|   | 1 | 2 | 3 | 4 | 5 | 6 |
|---|---|---|---|---|---|---|
| A | 008 | 568 | 580 | 000 |   |   |
| B | 267 | 538 | 539 | 547 |   |   |
| C | 656 | 530 | 729 | 822 |   |   |
| D | 848 | 570 | 605 |   |   |   |

↑ ↑ ↑
1 2 3 negative control 1 (DMEM full medium): 0.010
negative control 2 (DMEM, without FCS): 0.040
positive control 1 (mouse serum $1 \times 10^{-3}$): 0.723
positive control 2 (mouse serum $1 \times 10^{-2}$): >1500 a) The fusion of caryoplasts with mouse spleen cells led to in vitro multipliable, immunoglobulin-secreting cells. Although only a small part of the cytoplasm of the malignant partner had been introduced into the hybrid, it did not result in the possible extinction of the feature of "permanent growth".

b) The hybrid cells produced with caryoplasts synthesised and secreted mouse immunoglobulin in "hybridoma" quantities. The absence of the cytoplasm part of the Ag 8.653 consequently did not impair the production and secretion ability of the caryoplastsspleen cell hybrids.

c) From the fusion of cytoplasts with spleen cells, cell clones were also produced which proliferated in vitro and secreted antibodies. A satisfactory explanation for this especially surprising phenomenon is, at present, not known.

EXAMPLE 2

Cell fragmentation by means of glycerol lysis and fusion with human blood lymphocytes.

Material

Earle's balance salt solution (EBSS), culture medium PMI 1640, fetal calf serum (FCS) from Boehringer Mannheim GmbH, 8-azaguanine (8-Ag) of Serva (Heidelberg), agar (Bacto-agar 1614) of Difco (Hedinger KG, Stuttgart). The human plasmacytoma line HS SULTAN ATCC CRL-1484 was, as cryo-preserved cell material, thawed according to the ATCC procedure and taken into the culture.

According to the process described in Proc. Natl. Acad. Sci. USA, 71, 2679-2683/1974, $8 \times 10^7$ HS Sultan cells were cultured for 48 hours in 100 ml. RPMI full medium which contained 20 pM 8-Ag. The surviving cells were taken up in 10 ml. RPMI 1640 full medium without 8-Ag and multiplied for 10 days. The cells were then sown on to soft agar plates (P. Coffino et al., Proc. Natl. Acad. Sci. USA, 68, 219-223/1971), which had been produced with RPMI 1640 full medium + 20 μM 8-Ag (about 500 cells per Petri dish) and cultured in a carbon dioxide incubator. After 9 days, colonies growing in isolation were sterilely removed from the agar surface and multiplied in RPMI 1640 full medium + 8-Ag. A clone (called HS-SULTAN-8Ag-R1), which grew with a doubling time of about 20 hours, was used for the following experiment. The HS-R1cells were HAT-sensitive: cells which had been cultured in a density of 1 to $5 \times 10^5$ per ml. HAT medium (RPMI 1640 full medium with 0.1 mM hypoxanthine, 400 nM aminopterin and 31 μM thymidine), did not multiply and died completely within 7 days.

Human lymphocytes (from peripheral blood: PBL): 300 ml. venous blood were collected under sterile conditions in heparin solution (2 U/ml. blood) and the fraction of the mononuclear cells (MNC: lymphocytes, monocytes) isolated by standard methods. $3 \times 10^8$ MNC were suspended in 100 ml. RPMI 1640 + 10% FCS and, for the separation of the monocytes, incubated for 24 hours in culture vessels at 37° C. in 5% carbon dioxide atmosphere.

Methods

Fragmentation of HS-R1: The cells were laden with glycerol (according to the method of M. Jett et al., Isolation and characterisation of plasma membranes and intact nuclei from lymphoid cells, J. Biol. Chem., 252, 2134-2142/1977) and lysed by incubation in 10 mM tris-HCl buffer. The nuclei were separated off, by centrifuging at 200 g for 10 minutes at 4° C., from the membrane vesicles which, in turn, were sedimented by centrifuging at 5000 g for 40 minutes at 4° C.

Fusion

About $1 \times 10^8$ 729 HS-R1 nuclei were suspended with human lymphocytes in RPMI 1640 in the ratio of 1:1 and fused by means of PEG as described in Example 1, B.2.

The sediment of the membrane vesicle from about $1 \times 10^8$ HS-R1 cells was covered with a suspension of $1 \times 10^7$ human lymphocytes and fused by means of PEG.

In a control batch, about $2 \times 10^7$ HS-R1 nuclei were taken up in RPMI 1640 full medium (without HAT) and cultured in 4 24 Costar spot plates in a carbon dioxide incubator.

All fusionates and the control culture were cultured on mouse abdominal cavity macrophages, as described in Example-1, as feeder cells.

Detection of human Ig in culture supernatants: Microtitre ELISA as described in Example 1, B 2. For the coating, there was used immunoadsorptively purified antihuman-Ig from sheep. The same AB preparation was used for the preparation of the antihuman-IG-POD conjugate. The sheep AB reacted with all human Ig classes and did not show any crossreactivity with bovine or murine Ig.

Results

Fragmentation by glycerol-tris HCl lysis: The treatment broke up the HS-R1 cells into a nucleuscontaining fraction, which was sedimented at 200 g, and into a nucleus-free cytoplasma membrane vesicle fraction, which could be sedimented at 5000 g. Intact HS-R1 cells could not be recognised under the microscope in either of the two fractions. The nuclei were surrounded with more or less irregularly bounded cytoplasma strips Counting gave a nucleus yield of 85%. The vesicle fraction contained, besides a little debris, numerous 0.5 to 2 μm. sized vesicles without recognisable nucleus component parts.

The culture of $2 \times 10^7$ nuclei in RPMI full medium (without HAT) led, in an observation period of 12 weeks, to no growth of HD-R1 cells.

Culture of the fusionates: The nucleuslymphocyte and cytoplasm vesicle-lymphocyte fusionates were divided, respectively, on to 96 and 10 24 Costar spot plates and, in each case, half were cultured with and without HAT addition in RPMI full medium on mouse macrophages. From the second week after fusion, colonies of lymphoid cells were visible which continuously increased in size.

Production of human immunoglobulin: On day 21 after fusion, culture supernatants (on day 18, a complete change of medium was carried out) were tested for the content of human immunoglobulin. The results obtained are shown in the following Tables 2a and 2b:

TABLE 2

ELISA for the detection of human immunoglobulin in culture supernatants (caryoplast fusion, 21 days after fusion).

I + HAT

|   | 1 | 2 | 3 | 4 | 5 | 6 |
|---|---|---|---|---|---|---|
| A | 029 | 147 | 286 | 147 | 228 | 270 |
| B | 171 | 086 | 050 | 144 | 846 | 121 |
| C | 118 | 156 | 250 | 082 | 179 | 059 |
| D | 120 | 1148 | 024 | 096 | 023 | 151 |

I − HAT

|   | 1 | 2 | 3 | 4 | 5 | 6 |
|---|---|---|---|---|---|---|
| A | 660 | 233 | 175 | 270 | 410 | 322 |
| B | 103 | 264 | 229 | 253 | 271 | 260 |
| C | 045 | 343 | 370 | 128 | 150 | 126 |
| D | 171 | 173 | 141 | 116 | 218 | 699 |

II + HAT

|   | 1 | 2 | 3 | 4 | 5 | 6 |
|---|---|---|---|---|---|---|
| A | 135 | 290 | 107 | 279 | 530 | 674 |
| B | 116 | 500 | 469 | 315 | 315 | 627 |
| C | 120 | 050 | 068 | 159 | 226 | 145 |
| D | 191 | 078 | 686 | 110 | 242 | 561 |

II + HAT

|   | 1 | 2 | 3 | 4 | 5 | 6 |
|---|---|---|---|---|---|---|
| A | 381 | 235 | 489 | 514 | 608 | 217 |
| B | 348 | 239 | 214 | 158 | 367 | 163 |
| C | 185 | 275 | 235 | 234 | 322 | 316 |
| D | 219 | 202 | 292 | 283 | 220 | 052 | fusion, 21 days after fusion.

|   | 1 | 2 | 3 | 4 | 5 | 6 |
|---|---|---|---|---|---|---|
| A | 052 | 627 | 917 |   |   |   |
| B | 041 | 326 | 715 |   |   |   |
| C | 071 | 400 | 826 | 0889 |   |   |
| D | 079 | 917 | 494 | 1016 |   |   |

↑ 1  ↑ 2  ↑ 3

1 = nucleus control culture
2 = with HAT
3 = without HAT

If the extinction values of 0 to 99 are taken as being negative to doubtful, the values of from 100 to 200 as being positive and the values of >200 as being strongly positive, then, for the cultures produced by nuclear fusion, there is given the following distribution:

|  | ELISA on human immunoglobulin | | |
|---|---|---|---|
| nucleus-lymphocyte hybrids, cultivated | negative | positive | strongly positive |
| with HAT | | | |
| n (n = 48) | 11 | 18 | 19 |
| (%) | (23) | (37) | (40) |
| without HAT | | | |
| n (n = 48) | 2 | 12 | 34 |
| (%) | (4) | (25) | (71) |

The results permit the following to be recognised: fusionates which are produced with lysis fractions can be cultured without HAT selection. The process is very much less laborious than the cytochalasin B extrusion and gives fusable material in high yield. A clear separation into "nucleus" and "cytoplasma membrane" fractions is not achieved with either of the processes. Not only the fraction preponderantly containing nuclear material but also that preponderantly containing cytoplasm membrane vesicle produces, after fusion with human lymphocytes from the blood, in vitro multipliable, AB-producing cell clones.

The parallel batch of the nucleus-lymphocyte hybrids with and without HAT addition document the negative action of the selection medium: with HAT, 23% of the primary cultures are Ig negative and only 40% strongly positive; without HAT, more than 70% are strongly positive and only 4% Ig negative.

EXAMPLE 3

Fusion of spleen cells of an immunised mouse with native and fragmented myeloma cells Ag 8.653.

Material

Human thyroid-stimulating hormone (hTSH) and its isolated β-chain (β-hTSH) were obtained from Boehringer Mannheim- GmbH. Complete and incomplete Freund's adjuvant (CFA, IFA) from Difco, Methocal 1500 from Fluka and FITC covaspheres from Covalent Tech., co., Ann Arbor, Michigan, U.S.A.

was used a clone which formed antibodies against an unrelated antigen (mouse antidigoxin).

Results

Not only in the cultures from fusion 1 (with intact Ag 8.653 cells) but also those of fusion 2 (with Ag 8.653 lysis fragments), on day 14 in all spots colonies of large, lymphoid cells were recognisable. The ELISA carried out with culture supernatants from day 14 for the detection of TSH-specific antibodies gave the values summarised in the following Table 3: anti-TSH was detected in all part cultures.

TABLE 3

ELISA for the detection of anti-TSH in culture supernatants on day 14 after fusion. a) fusion 1 (intact Ag 8.643), b) fusion 2 (Ag 8.653 fragments).

| a) | 1 | 2 | 3 | 4 | 5 | 6 | b) | 1 | 2 | 3 | 4 | 5 | 6 |
|---|---|---|---|---|---|---|---|---|---|---|---|---|---|
| A | 235 | 236 | 212 | 149 | 119 | 212 | A | 271 | 268 | 267 | 286 | 194 | 291 |
| B | 109 | 221 | 119 | 104 | 176 | 068 | B | 288 | 278 | 362 | 317 | 280 | 305 |
| C | 116 | 108 | 135 | 139 | 093 | 135 | C | 207 | 292 | 252 | 226 | 292 | 271 |
| D | 171 | 128 | 120 | 228 | 137 | 145 | D | 295 | 376 | 370 | 338 | 310 | 333 | negative control (DMEM full medium): 000
positive control (anti-TSH mouse serum): 362

Methods

Immunisation: Balb/c mice were primarily immunised with β-hTSH (40 μg. in CFA, intraperitoneally) (day 1) and on day 196 boosted with hTSH (50 μg. in IFA, i.p.), on day 266 with hTSH without adjuvant i.p., as well as on day 294 with hTSH intravenously.

Spleen cells (about $1 \times 10^8$) were obtained from one of the immunised mice 3 days after the last booster immunisation, as described in Example 1, B.2, and halves thereof used for two fusions. Fusion 1: $5 \times 10^7$ spleen cells and $1 \times 10^7$ Ag 8.653 cells were mixed, fused as described in Example 1, B.2, and cultured in 48 24 spot plates with mouse macrophage cells in HAT-containing DMEM full medium. Fusion 2: $1 \times 10^7$ Ag 8.653 cells were lysed as described in Example 2 by stepwise treatment with glycerol and 10 mM tris-HCl buffer. The cytoplasmamembrane vesicle (CMV) fraction was pelleted (5000 g, 40 minutes, 4° C.). The nucleus fraction was mixed with $7 \times 10^7$ spleen cells, layered by centrifuging on the CMV sediment and fused by means of PEG according to the standard process as described in Example 1, B.2.The fusionate was divided up in DMEM full medium on to 24 24 Costar spot plates with macrophages and cultured without the addition of HAT. Antigen-specific labeling of hybrid cells and cloning: (FITC) Covaspheres were coated covalently with hTSH according to the general instructions of the manufacturer (TSH-CS) and stored in 0.5% sodium azide solution. According to the process described by D. R. Parks (Proc. Natl. Acad. Sci. USA, 76, 1982–1966/1979), the cells were labeled with the coated Covaspheres and, with the help of a cytofluorograph, large, fluorescence-positive cells were "placed" individually in spot plates and 96 Costar plates. The spot plates had been coated 24 hours previously with mouse macrophages in DMEM full medium. ELISA for TSH-specific antibodies: Coating, incubation of the culture supernatants, substrate reaction and reading off as described in Example 1, B.2. Instead of antimouse-Ig-POD, there was used TSH-POD conjugate. As positive control, there was used serum of an hTSH-hyperimmunised mouse, diluted $10^{-3}$; as negative control, there On day 15, the non-adherent cells were rinsed out of the individual spots of fusion 1 and 2 and TSH antigen-specifically labeled in separated batches. (basis: hybridomas carry, as a rule, like B-lymphocytes, a part of the antibody molecules synthesised by them anchored in the cell membrane, with "outwardly" directed antigen combining sites) and cloned with the help of the cell sorter.

EXAMPLE 4

Fusion of human PBL with intact and with fragmented Ag 8.653 cells.

Material

Inactivated hepatitis-B antigen ($HB_{sf}$, Biotest) was purified from serum proteins by immunoadsorption. ELISA for the detection of human $HB_s$-antibodies: microtiter plates were coated with purified $HB_{si}$ (20 μg./ml. 0.9% sodium chloride solution). Incubation of the culture supernatants, conjugate and substrate reaction, as well as reading off, as described in Example 1, B.2. Instead of anti-mouse Ig-POD, there was used (sheep) anti-human Ig-POD.

Methods

HPBL from a donor with high anti-HBs titre were isolated ±rom 200 ml. venous blood by Ficoll gradient centrifuging. For the enrichment of the B-lymphocytes, the T-cells were rosetted with sheep erythrocytes (according to the standard process) and separated by means of a second Ficoll gradient centrifuging. The fraction of the non-rosetting cells (HPBL(B)) were cultured at a density of $5 \times 10^7$ cells in RPMI 1640+10% autologous plasma (30 minutes/56° C.heat-inactivated) with about 10μg/ml $HB_{si}$ in a carbon dioxide incubator (medium change every 12 hours). Fusion 1: $1 \times 10^7$ of the pre-treated HPBL(B) were mixed with $1 \times 10^7$ Ag 8.653 and fused by means of PEG as described in Example 1, B 2. The fusionate was cultured in RPMI 1640+10% human plasma+HAT in 4 24 Costar spot plates.

Fusion 2: $1.1 \times 10^8$ Ag 8.653 cells were fragmented by means of glycerol lysis. $1 \times 10^7$ Ag 8.653 nuclei were mixed with $1 \times 10^7$ HPBL(B) and coated on to the sediment of membrane cytoplasm vesicles (from $1 \times 10^8$ Ag 8.653 cells). After fusion with PEG, the fusionate was cultured in 4 24 Costar spot plates in RPMI 1640+10% human plasma (without HAT adddition).

Results

In all spots of fusion 1 and 2, from day 3 there appeared the growth of very large, adherent cells. On day 5, the main mass of the non-adherent cells was carefully suspended and distributed on two new 24 Costar spot plates (for example A1, B1 and C1). On day 28 in fusion 1: no colonies in A2 and A3, in the remaining spot plates only adherent cells; in fusion 2: massive growth of multiple colonies in all spots with the exception of C3. The ELISA carried out with culture supernatants from day 35 for the detection of human immunoglubulins with specificity against hepatitis-B antigen gave the results summarised in the following Table 4: fusion 1 (intact Ag 8.653 cells, culture in HAT medium) did not give a positive culture; on the other hand, 5 to 12 cultures of fusion 2 (Ag 8.653 fragments, culture in normal medium) were clearly anti-$HB_s$ positive.

TABLE 4

ELISA for the detection of human anti-$HB_s$ in culture supernatants on day 35 after fusion: a) fusion 1 (intact Ag 8.653), b) fusion 2 (Ag 8.653 fragments)

a)

|   | 1   | 2   | 3   | 4   |
|---|-----|-----|-----|-----|
| A | 000 | 000 | 000 | 000 |
| B | 000 | 001 | 011 | 000 |
| C | 005 | 000 | 000 | 004 | b)

|   | 1   | 2   | 3   | 4   |
|---|-----|-----|-----|-----|
| A | 010 | 000 | 189 | 553 |
| B | 000 | 003 | 198 | 032 |
| C | 000 | 173 | 000 | 107 | negative control (anti-$HB_s$-neg. human serum): 000
positive control (anti-$HB_s$-pos. human serum): 185

EXAMPLE 5

Fusion of HPBL fragments from the human plasma cytoma line HS SULTAN

Material

HS Sultan was obtained from the American Type Culture collection (ATCC) under the code CRL-1484 as cryo-preserved cell material and thawed out according to the ATCC procedure and taken up in the culture.

Methods

HPBL was, as described in Example 4, prepared from the same donor and boostered in vitro with $HB_{si}$. Fusion: $4 \times 10^7$ HS SULTAN cells were fragmented by means of glycerol lysis. The membrane-cytoplasm fraction was sedimented at 5500 g (40 minutes) and a mixture of about $4 \times 10^7$ HS-SULTAN nuclei and $4 \times 10^7$ HPBL(B) coated thereon. PEG fusion took place according to Example 4. Seeding out of the fusionate on 12 24 Costar spot plates in RPMI 1640+20% FCS+pyruvate+insulin (Novo 2U/ml.)+1% non-essential amino acids (BM)+1% Methocel 1500 without HAT addition.

Results

Day 14 after fusion: growth of large, nonadhering lymphoid cell colonies.

EXAMPLE 6

Immortalisation of human T-lymphocytes.

6.1. Material and methods.

T-lymphocytes were isolated by means of standard processes (rosetting with sheep erythrocytes, Ficoll gradient centrifuging) from the lymphocyte whole fraction and treated immediately or after culturing for 3 days. Ehrlich ascites cells (ATCC; CCL 77) were cultured in DMEM with 10% horse serum and served as donor of the transforming fragments. The fragmentation of the EAC was carried out according to the method of Jett et al. (J. Biol. Chem., 252, 2134–2142/1977) by means of glycerol lysis. The fraction preponderantly containing nuclear material was separated by centrifuging and discarded. The mitochondriarich cytoplasmic membrane vesicle fraction (CMV) was used for the transforming. $5 \times 10^7$ T-lymphocytes were loaded with an excess of PHA lectin (Difco), mixed with the CMV fraction from EAC and incubated for 20 minutes at ambient temperature. The mixture was sedimented by centrifuging and the liquid supernatant completely removed and replaced by 1 ml. of a 50% PEG solution. After an action time of 1 minute, the PEG solution was diluted by the addition of RPMI 1640 culture medium and separated from the cells by centrifuging. The cells were taken up in RPMI medium with 20% fetal calf serum (FCS, BM), distributed on to 12 1 ml. culture spot plates and cultured at 37° C. in 5% carbon dioxide atmosphere. The characterisation of the cells on the basis of the surface characteristics took place according to standard processes by means of sheep erythrocyte (E) rosetting (see M. E. Kaplan et al., J. Immunol. Methods, 5, 131/1974) and by means of immunofluorescence with the use of the two T cell-specific antibodies OKT-3 (Ortho; E.L. Reinherz et al., J. Immunol., 123, 1312/1979) or MAK 4-11 (P. Rieber et al., Hybridoma, 1, 59/1981) and fluorescencemarked anti-human serum immunoglobulin (Ig, Dako) for the detection of B-cell-typical membrane Ig.

6.2. Results

Within the first 14 days, the greater part of the cells in the cultures died. From day 21, in the cell debris there were visible colonies of small to medium-large cells which multiplied continuously. Growth of colonies was found in all 12 spots, namely, up to 50 colonies per spot. On day 30, the colonies were transferred to larger culture vessels and further multiplied. The cells were analysed on the basis of their surface marker and the following results were obtained:

| a) E rosette-positive | >95% |
|---|---|
| b) OCT-3-positive | >90% |
| c) 4-11-positive | >90% |
| d) $Ig_s$-positive | <5% |

6.3. Assessment

Fragments which can be obtained from EAC (permanent mouse cell line) by glycerol lysis produced, after PEG fusion with isolated T-lymphocytes, cells which grow permanently in culture which, on the basis of their surface characteristics, are clearly identifiable as T-lymphocytes.

EXAMPLE 7

Immortalisation of human endothelial cells.

7.1. Material and methods

Before seeding with cells, all culture vessels were coated with gelatin. The culture medium consisted of 1:1 mixture of RPMI-1640 and medium 199 (BM) with 20% FCS. Human endothelial cells were obtained according to the method of Jaffe et al. (J. Clin. Invest., 52, 2745-2756/1973) by means of collagenase solution (Gibco) from the veins of fresh umbilical cords and, before the transformation, by laying on of a primary culture, multiplied for about 14 days. For the transformation, the adherently growing endothelial cells were separated off by means of trypsin-EDTA solution (BM) and fused in suspension, as described in Example 6.1, with the CMV fraction from EAC. The so-treated cells were shown in cell density of $5 \times 10^5$ per 75 $cm^2$ culture vessel and cultured in a carbon dioxide incubator. For the control, there were, in each case, treated an aliquot of the endothelial cells from the primary culture without CMV fraction with PEG solution (simulated fusion) and recultured. As soon as the cells had formed a confluent cell deposit on the bottom of the culture vessel, they were dissolved off by means of trypsin-EDTA solution and transferred in a ratio of 3:1 to fresh culture vessels (=passage).

7.2. Results

The endothelial cells fused with CMV fraction adhered, after sowing in, with an efficiency of 20 to 30% and grew within the course of 2 to 3 days to give a confluent cell layer. The simulated fused cells adhered with about the same efficiency, but hardly multiplied and died completely, without forming a confluent cell layer within about 21 days. Completely untreated endothelial cells multiplied up to a maximum in the 3rd passage. Growth then ceased, they loosen from the bottom of the culture vessel with spheroidal formation and are lysed. In 8 different batches with endothelial cells from a total of 18 different umbilical cords, the CMV-treated cells grew without problems beyond the 10th passage. The transformed endothelial cells could be stored in and taken from liquid nitrogen without loss of viability and ability to multiply.

7.3. Assessment

Human umbilical endothelial cells could, without transforming manipulation according to the present invention, not be cultured beyond the 3rd passage, which confirmed the experiences reported in the literature (see, for example, M. A. Grimbrone in Progress in Haemostasis and Thrombosis, Vol. 3; T. Maciag et al., J. Cell. Biol., 91, 420–426/1981). By fusion with the mitochondria-rich CMV fraction from Ehrlich ascites cells, the culture properties of the endothelial cells were so changed that they multiplied without problems beyond the critical 3rd passage (and are, at present, in the 23rd passage, without showing "fatigue phenomena").

EXAMPLE 8

Immortalisation of human melanoma cells

8.1. Material and methods

Melanoma cell-containing tissue was obtained by surgical excision of a hip lymph nodule metastasis, cut up into small cubes under sterile conditions and stored in liquid nitrogen until fusion. CMV fractions from EAC were prepared as described in Example 6.1.

Before the fusion, the melanoma cell-containing material was thawed and, by means of a trypsin treatment, a single cell suspension was produced. The large, brown-red pigmented melanoma cell fraction was freed by Ficoll gradient centrifuging from accompanying lymphocytes and, as described in Example 6.1, fused with CMV fraction under the influence of PEG (about $4 \times 10^5$ melanoma cells with CMV from about $1 \times 10^6$ EAC). For control of the fusion, there were used $4 \times 10^5$ melanoma cells which had been treated with PEG without CMV. After fusion, the cells were sown in a density of $1 \times 10^5$ cells per spot in RPMI 1640+20% FCS and cultured at 37° C. in 5% carbon dioxide atmosphere.

8.2. Results

In all 4 part cultures of the melanoma cells fused with CMV, from day 28 there grew colonies of typically pigmented cells in the form of semiadhering cell heaps which increased continuously. In the control culture of the simulated fused cells, no cell multiplication occurred; on the contrary, from day 8, the cells showed an increasing granulation and on day 22 only cell debris was still present in the culture.

8.3. Assessment

Human melanoma cells from cryo-preserved metastatic tissue could be transformed by CMV fusion into cells which could be cultured and multiply in vitro. On the other hand, simulated fused melanoma cells of the same origin died under otherwise identical culture conditions.

EXAMPLE 9

Introduction of an eucaryotic DNA-vector into immortalized human endothelial cells

9.1 Detection of transfected material in the cells by Southern blotting of Hirt supernatants

9.1.1 Materials

Plasmid Z-pBR 322/Rchr$\beta$G-$\Delta$ 425 B (Dierks, P. et al., Proc. Natl. Acad. Sci. USA 78, 1411–1415 (1981)) contains a 2070 bp rabbit $\beta$-globin gene fragment. The Cla-Pvu I fragment of pBR 322 was replaced by a 3039 bp Hpa I-Bam H 1 fragment containing the whole early region and the beginning of the late region of SV 40 (Tooze, J. (1980), in "DNA Tumor Viruses", J. Tooze, ed., 2nd edition, Cold Spring Harbor Laboratory and B. Wieringa et el., Cetus-UCLA Symposium on Gene regulation 1982)). This plasmid will be referred to as pBR 322 R$\beta$G SV 40.

9.1.2 Methods

Human endothelial cells were immortalized and propagated as described in example 7. $10^6$ cells each were transfected with 6 $\mu$g pBR 322 R$\beta$G SV 40 and 4 $\mu$g sonicated calf thymus DNA by the Calcium-phosphate precipitation method (Graham, F. L. et al., Virology 52, 456–467 (1973) and Wigler, M. et al., Cell 14, 725–731 (1978)). 10 hrs and 40 hrs after transfection, Hirt supernatants were prepared (Hirt, B., J. Mol. Biol. 26, 365–369 (1967)).

The Hirt supernatants were separated on a 1% agarose gel and transferred to nitrocellulose paper by the procedure of Southern (Southern, E. M., J. Mol. Biol. 98, 503–517 (1975)). Plasmid pBR 322 R$\beta$G SV 40 was labeled with $^{32}P$ by the nick translation procedure of Rigby, P. W. et al., J. Mol. Biol. 113, 237–251 (1977) and hybridized with the transferred DNA on the nitrocellulose filters, all as described in (Maniatis, T. et al., Molecular Cloning, Cold Spring Harbor Laboratory (1982)). The filter was exposed to X-ray film at −70° C.

9.1.3 Results

Human endothelial cells transfected with plasmid pBR 322 RβG SV 40 gave rise to a strong hybridization signal corresponding to authentic plasmid with respect to its mobility on an agarose gel. A four to five fold increase in the intensity of the hybridization signal was observed comparing the signals of the Hirt supernatants from cells 10 hrs and 40 hrs after transfection. Hybridization to DNA species smaller than the input plasmid also was observed. These signals were not detectable in non-transfected immortalized human endothelial cells. The same distribution of the intensity of the hybridization signals was observed when HeLa cells were transfected with plasmid pBR 322 RβG SV 40.

9.1.4 Conclusions

The fact that DNA hybridizing to $^{32}$P-labeled input plasmid could be detected in the Hirt supernatants of human immortalized endothelial cells transfected with plasmid pBR 322 RβG SV 40 and not in non-transfected cells is good evidence the eucaryotic cell line. The observation that the hybridization signal from transfected cells corresponding to 40 hrs after transfection was 4–5 fold increased in intensity compared to that of cells corresponding to 10 hrs after transfection supports the conclusion that the transfected plasmid has been replicated in the cells.

9.2 Detection of rabbit β-globin specific transcripts in immortalized human endothelial cells transfected with plasmid pBR 322 RβG SV 40

9.2.1 Materials

Nuclease S$_1$, T$_4$ polynucleotide kinase and calf-intestine phosphatase were those commercially available from Boehringer Mannheim, F.R.G.

9.2.2 Methods

Human endothelial cells (immortalized) were propagated and transfected with the rabbit β-globin gene containing vector as described in 9.1.2. 48 hrs after the transfection 1–2×10$^6$ cells were lysed the RNA extracted by the LiCl-urea method (Auffray, C. at al., Eur. J. Biochem. 107, 303–314 (1980)).

Preparation of a rabbit β-globin specific hybridization probe

Plasmid pBR 322 RβG SV 40 was digested with Hae III and the fragment extending from +135 to −75 (Dierks, P. et al., Proc. Natl. Acad. Sci. USA 78, 1411–1415 (1981) and Van Oyen, A. et al., Science 206, 337–344 (19) was isolated on a 2% agarose gel and further perified by DEAE-cellulose chromatography (Müller, W. et al., J. Mol. Biol. 124, 343–358 (1978)). The fragment was dephosphorylated with calf-intestine phosphatase and $^{32}$P- and labeled with γ-$^{32}$P-ATP and T$_4$ polynucleotide kinase, all as described in (Mantei, N. et al., Gene 10, 1–8 (1980)).

Nuclease S$_1$ mapping

The kinased fragment was ethanol precipitated together with 10 μg E. coli t-RNA (Boehringer Mannheim) and dissolved in 100 μl 0.4 M/l NaCl, 1 mM/l EDTA, 40 mM/l PIPES, pH 6.4 and 80% formamide (Mantei, N. et al., Nature 281, 40–46 (1979)). Cellular RNA (=25 μg) was vacuum-dried, dissolved in 10 μl probe (0.01 pMol, 30.000 cpm) in buffer as described above, denatured, melted into glass capillaries and hybridized at 48° C. for 16 hrs. In a control experiment the probe was hybridized to rabbit β-globin messenger RNA (Miles). The sample was diluted with 100 μl 0.2 M/l NaCl, 50 mM/l sodium-acetate (pH 4.5), 1 mM/l ZnSO$_4$, 0.5% glycerol and incubated with 50 units of nuclease S$_1$ for 60 minutes at 30° C. (Weaver, R. et al., Nucl. Acid Res. 7, 1175–1193 (1979)). The samples were phenolized, ethanol precipitated with 10 μg of E. coli t-RNA, washed with 80% ethanol (20 minutes at −170° C), vacuum-dried, dissolved in 5 μl of loading solution (0.05% bromphenol blue, 0.05% xylenexyanol, 1 mM/l EDTA, 90% (v/v) formamide, heated for 2 minutes in a boiling water bath and electrophoresed on a 5% polyacrylamide gel (89 mM/l TRIS base, 89 mM/l boric acid, 1 mM/l EDTA and 7 M/l urea). The gel was autoradiographed with Fuji X-ray film and an intensifying screen at −70° C.

9.2.3 Results

The size of the protected fragments could be evaluated by comparison to size markers ($^{32}$P-labeled pBR 322×Hinf 1 and pBR 322×Hae III). Untransfected cells did not give rise to any globin specific hybridization signal (with the exception of renatured hybridization probe=210 bp). RNA extracted from transfected immortalized human endothelial cells protected two fragments, the size of which was determined to be 80–90 bp. Such transcripts also were found by Grosveld et al., Nature 295, 120–126 (1982)) and Weidle, U. et al., Nature (1981) are attributed to the presence of an internal cryptic splice site on the rabbit β-globin gene. Transcripts originating from the cap site of the rabbit β-globin gene could not be detected. In a control experiment, HeLa cells were transfected with plasmid pBR 322 RβG SV 40. Correctly initiated transcripts (135 bp protected) as well as transcripts attributed to the presence of an internal cryptic splice site (Grosveld, G. et al., Nature 295, 120–126 (1982)) and Weidle, U. et al., Nature (1983) were evaluated by S$_1$-mapping.

9.2.4 Conclusions

The fact that rabbit β-globin specific transcripts are detectable in immortalized human endothelial cells transfected with an SV 40 based eucaryotic vector containing the rabbit β-globin gene clearly indicates that this cell line is a host system for the expression of reintroduced cloned genes.

We claim:

1. A process for obtaining animal and human cells which are permanently culturable in vitro, comprising the steps of:
   (a) fusing normal animal or human cells with cytoplasts or cytoplasm fractions which are incapable of multiplying and which are obtained from transformed cells; and
   (b) cultivating the fused product of step (a) in non-selective medium to obtain permanently culturable cells.

2. A process according to claim 1, wherein fusion takes place in the presence of polyethylene glycol or Sendai virus.

3. A process according to claim 1, wherein said cytoplasts or cytoplasm fractions are obtained from transformed cells treated with cytochalasin B.

4. A process according to claim 1, wherein said cytoplasts or cytoplasm fractions are obtained by lysis or mechanical digestion of transformed cells.

5. A process according to claim 1, wherein said cytoplasts or cytoplasm fractions are cytoplasts or cytoplasm fractions of myeloma cells, ascites tumor cells or Epstein-Barr virus infected cells.

6. A method of obtaining a cell product from the permanently culturable cells of claim 1, comprising culturing said cells under conditions favoring production of a cell product therefrom, and separating said product from said cells.

7. A permanently culturable cell line comprising cells derived from the fusion of normal human or animal cells with cytoplasts or cytoplasm fractions from transformed cells.

* * * * *

UNITED STATES PATENT AND TRADEMARK OFFICE
CERTIFICATE OF CORRECTION

PATENT NO. : 5,114,847
DATED : May 19, 1992
INVENTOR(S) : Herbert Jungfer et al.

It is certified that error appears in the above-identified patent and that said Letters Patent is hereby corrected as shown below:

Column 3, line 3: change "106" to -- $10^6$ --.

Column 6, line 9: change "i-s" to -- is --.

Column 7, line 60: before "B-lymphocytes" insert -- + --.

Column 12, line 10, change "PMI 1640" to --RPMI 1640-- line 20: change "20pM" to -- 20 um --.

Column 13, line 40, change "IG-POD" to --Ig-POD--

Column 17, line 1: change "108" to -- $10^8$ --.

Signed and Sealed this

Seventh Day of December, 1993

*Attest:*

BRUCE LEHMAN

*Attesting Officer*  *Commissioner of Patents and Trademarks*